United States Patent [19]

Sanderson et al.

[11] Patent Number: 5,243,101
[45] Date of Patent: Sep. 7, 1993

[54] REMOVAL OF PEROXIDE CONTAMINANTS FROM TERTIARY BUTYL ALCOHOL

[75] Inventors: John R. Sanderson, Leander; Yu-Hwa E. Sheu; Michael W. Peters, both of Austin, all of Tex.

[73] Assignee: Texaco Chemical Company, White Plains, N.Y.

[21] Appl. No.: 896,859

[22] Filed: Jun. 12, 1992

[51] Int. Cl.$^5$ .................. C07C 29/76; C07C 31/12
[52] U.S. Cl. ........................ 568/913; 563/909.8
[58] Field of Search ......................... 568/909.8, 913

[56] References Cited

U.S. PATENT DOCUMENTS

| | | | |
|---|---|---|---|
| 2,633,426 | 12/1953 | Wilson et al. | 568/917 |
| 2,663,745 | 12/1953 | Wilson | 568/917 |
| 4,704,482 | 11/1987 | Sanderson et al. | 568/922 |

Primary Examiner—Joseph E. Evans
Attorney, Agent, or Firm—Jack H. Park; Kenneth R. Priem; Carl G. Ries

[57] ABSTRACT

Motor-fuel tertiary butyl alcohol contaminated with residual amounts of tertiary butyl hydroperoxide, ditertiary butyl peroxide and allyl tertiary butyl peroxide (which is prepared, for example, by reacting propylene with tertiary butyl hydroperoxide to form propylene oxide and a motor fuel grade tertiary butyl alcohol reaction product) can be effectively catalytically treated under mild conversion conditions including a temperature of about 160° to 200° C. with a catalyst consisting essentially of vitrified silica to substantially completely decompose the peroxide contaminants to thereby provide a treated tertiary butyl alcohol product substantially free from contaminating quantities of such peroxides.

4 Claims, No Drawings

REMOVAL OF PEROXIDE CONTAMINANTS FROM TERTIARY BUTYL ALCOHOL

BACKGROUND OF THE INVENTION

1. Field of the Invention

This invention relates to a method for the removal of residual contaminating quantities of tertiary butyl hydroperoxide, allyl tertiary butyl peroxide and ditertiary butyl peroxide from a tertiary butyl alcohol feedstock to provide a tert. butyl alcohol product which is useful as an octane-enhancing component for motor fuels. In accordance with the present invention the peroxide-contaminated feedstock is brought into contact with a catalyst consisting essentially of particulate vitrified silica (glass beads) in order to substantially selectively reduce the amount of tertiary butyl hydroperoxide, ditertiary butyl peroxide and allyl tertiary peroxide in the tertiary butyl alcohol.

2. Prior Art

A process for the manufacture of substituted epoxides from alpha olefins such as propylene is disclosed in Kollar U.S. Pat. No. 3,351,653 which teaches that an organic epoxide compound can be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. When the olefin is propylene and the hydroperoxide is tertiary butyl hydroperoxide, propylene oxide and tertiary butyl alcohol are coproducts. U.S. Pat. No. 3,350,422 teaches a similar process using a soluble vanadium catalyst. Molybdenum is the preferred catalyst. A substantial excess of olefin relative to the hydroperoxide is taught as the normal procedure for the reaction. See also U.S. Pat. No. 3,526,645 which teaches the slow addition of organic hydroperoxide to an excess of olefin as preferred.

Stein, et al. in U.S. Pat. No. 3,849,451 have improved upon the Kollar process of U.S. Pat. Nos. 3,350,422 and 3,351,635 by requiring a close control of the reaction temperature, between 90-200° C. and autogenous pressures, among other parameters. Stein et al. also suggests the use of several reaction vessels with a somewhat higher temperature in the last vessel to ensure more complete reaction. The primary benefits are stated to be improved yields and reduced side reactions.

It is known that isobutane can be oxidized with molecular oxygen to form a corresponding tertiary butyl hydroperoxide and that the oxidation reaction can be promoted, for example with an oxidation catalyst (see Johnston U.S. Pat. No. 3,825,605 and Worrell U.S. Pat. No. 4,296,263.

Thus, tertiary butyl alcohol can be prepared either by the direct thermal or catalytic reduction of tertiary butyl hydroperoxide to tertiary butyl alcohol or by the catalytic reaction of propylene with tertiary butyl hydroperoxide to provide propylene oxide and tertiary butyl alcohol.

It is also known that tertiary butyl alcohol can be used as an octane-enhancing component when added to a motor fuel, such as gasoline. Thus, it has heretofore been proposed, as shown, for example, by Grane U.S. Pat. No. 3,474,151 to thermally decompose tertiary butyl hydroperoxide to form tertiary butyl alcohol to be used as an octane-enhancing component of a motor fuel. Grane points out that the thermal decomposition must be conducted with care because tertiary butyl alcohol will start to dehydrate at a temperature of about 450° F. (about 232° C.) and in that dehydration becomes rapid at temperatures above about 475° F. (about 246° C.). Grane also points out that the tertiary butyl alcohol prepared in this manner will contain contaminating quantities of ditertiary butyl peroxide. Ditertiary butyl peroxide is more refractory than tertiary butyl hydroperoxide and adversely affects the octane-enhancing qualities of tertiary butyl alcohol. Grane discovered that the residual contaminating quantities of ditertiary butyl peroxide could be removed from the tertiary butyl alcohol by thermally treating the contaminated tertiary butyl alcohol at a temperature of 375° F. to 475° F. (about 190° to about 244° C.) for a time of from 1 to 10 minutes.

This concept was expanded upon by Grane et al. in U.S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. (about 148.8° C.) for several hours to significantly reduce the concentration of the tertiary butyl hydroperoxide. However, the product of this thermal decomposition step still contained residual tertiary butyl hydroperoxide, most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide and ditertiary butyl peroxide from motor grade tertiary butyl alcohol has received appreciable attention. Ditertiary butyl peroxide is the more refractory of the two peroxides. Another refractory peroxide that is frequently present as a contaminant is allyl tertiary butyl peroxide. Allyl tertiary butyl peroxide is more refractory than tertiary butyl hydroperoxide but less refractory than ditertiary butyl peroxide.

The problems encountered in attempting the thermal removal of contaminating quantities of peroxides such as allyl tertiary butyl peroxide and ditertiary butyl peroxide from tertiary butyl alcohol have led to the provision of a variety of catalytic processes for removing contaminating quantities of peroxides such as allyl tertiary butyl peroxide and ditertiary butyl peroxide from tertiary butyl alcohol as exemplified, for example, by Sanderson et al. U.S. Pat. No. 4,547,598, U.S. Pat. No. 4,704,482, U.S. Pat. No. 4,705,903, U.S. Pat. No. 4,742,179, U.S. Pat. No. 4,873,390, U.S. Pat. No. 4,910,349, U.S. Pat. No. 4,912,266, U.S. Pat. No. 4,912,267, U.S. Pat. No. 4,922,033, U.S. Pat. No. 4,922,034, U.S. Pat. No. 4,922,035, U.S. Pat. No. 4,922,036, etc.

In some instances, it is proposed to use silica as a support for the catalyst, e.g., Sanderson et al. U.S. Pat. No. 4,704,482, U.S. Pat. No. 4,705,903, U.S. Pat. No. 4,742,179, U.S. Pat. No. 4,873,380, etc. The silica when used as a support is normally used in an un-vitrified high surface area form, such as Kieselguhr.

SUMMARY OF THE INVENTION

The feedstocks of the present invention comprise tertiary butyl alcohol contaminated with tertiary butyl hydroperoxide, ditertiary butyl peroxide and, frequently, allyl tertiary peroxide.

When isobutane is treated to form tertiary butyl hydroperoxide, the reaction product will normally contain some tertiary butyl alcohol and other oxygenated by-products such as ditertiary butyl peroxide, allyl tertiary butyl peroxide, etc., as well as unreacted isobutane. After the unreacted isobutane is removed, a fraction composed mostly of tertiary butyl alcohol may be recovered as a distillate fraction. The tertiary butyl alcohol distillate, which will normally be contaminated with tertiary butyl hydroperoxide, ditertiary butyl peroxide, allyl tertiary peroxide, etc., may be used as a feedstock for the process of the present invention.

Tertiary butyl hydroperoxide is suitably reacted with propylene by a process of the type disclosed in Kollar U.S. Pat. No. 3,351,635 to provide an initial reaction product composed mostly of unreacted propylene, propylene oxide and tertiary butyl alcohol. However, residual quantities of tertiary butyl hydroperoxide and ditertiary butyl peroxide and other oxygenated impurities are normally present and remain dissolved in the tertiary butyl alcohol recovered from the reaction mixture. This tertiary butyl alcohol product can also be used as a feedstock for the process of the present invention.

It has been surprisingly discovered in accordance with the present invention that a feedstock comprising tertiary butyl alcohol contaminated with minor amounts of peroxide impurities such as tertiary butyl hydroperoxide, ditertiary butyl peroxide, allyl tertiary butyl peroxide, etc., can be effectively treated without significant dehydration of the tertiary butyl alcohol by bringing the peroxide-contaminated feedstock into contact with vitrified silica in a continuous process conducted at a temperature of about 160° C. to about 180° C. at a space velocity of about 100 to about 400 cc of feedstock per hour per 100 cc of reactor volume and a pressure of about 0 to about 2,000 psig.

In accordance with the present invention, a peroxides-contaminated tert. butyl alcohol feedstock such as a feedstock contaminated with tert. butyl hydroperoxide, ditertiary butyl peroxide, allyl tertiary peroxide, etc., is brought into contact with a catalyst of the present invention under mild conditions including a temperature of about 160° to 180° C. and a pressure sufficient to maintain a liquid phase reaction mixture (normally, about 200 to 800 psig., depending on reaction temperature). Higher pressures of up to about 2000 psig. can be used, if desired, but there is no particular advantage in using the higher pressures. This treatment will substantially selectively decompose the peroxide contaminants and thereby provide a treated product substantially free of contaminating quantities of tertiary butyl hydroperoxide and ditertiary butyl peroxide.

The results obtained with the process of the present invention are surprising and unexpected in several respects. Silica is normally considered to be an inert material useful as a support for catalytically active metals, such as transition metals. It has been discovered in accordance with the present invention that vitrified silica has a slight catalytic activity in respect of the decomposition of peroxides such as tertiary butyl hydroperoxide, ditertiary butyl peroxide, allyl tertiary butyl peroxide, etc., which permits effective decomposition of these impurities at temperatures below the temperature range specified in the prior art for effective thermal decomposition of the peroxide contaminants present in tertiary butyl alcohol.

The decomposition of the peroxide contaminants is substantially quantitative, conversion of the peroxides normally ranging from about 95 to about 100%. Also, there is good selectivity in that tertiary butyl alcohol is the principle decomposition product.

Thus, the provision of the process of the present invention wherein a motor-fuel grade tertiary butyl alcohol feedstock containing contaminating quantities of ditertiary butyl peroxide, tertiary butyl hydroperoxide, etc., is catalytically treated for the decomposition of the peroxides results in their substantially complete removal from the treated feedstock.

STARTING MATERIALS

The starting materials for the process of the present invention include a motor-fuel grade tertiary butyl alcohol feedstock obtained in the manner described above by the reaction of propylene with tertiary butyl hydroperoxide to form propylene oxide and tertiary butyl alcohol by the oxidation of isobutane to form tertiary butyl hydroperoxide, etc.

The motor-fuel grade tertiary butyl alcohol feedstock obtained by the reaction of propylene with tertiary butyl hydroperoxide to form propylene oxide and tertiary butyl alcohol will contain contaminating quantities of tertiary butyl hydroperoxide, ditertiary butyl peroxide, allyl tertiary butyl peroxide, etc., and acetone. The normal levels of contamination of such materials are such that the tertiary butyl alcohol will normally contain, prior to treatment, from about 0.0 to about 1 wt. % of tertiary butyl hydroperoxide, from about 0.1 to about 5 wt. % of ditertiary butyl peroxide and about 0.05 to about 2.5 wt. % of allyl tertiary butyl peroxide. Minor quantities of other peroxide contaminants may also be present.

As indicated earlier, the reaction conditions used in the catalytic oxidation of isobutane will sometimes result in the formation of ditertiary butyl peroxide. Thus, the feedstock to be used for the practice of the present invention is an impure motor grade tertiary butyl alcohol containing from about 0.0 to about 1 wt. % of tertiary butyl hydroperoxide and from about 0.1 to about 5 wt. % of ditertiary butyl peroxide.

The catalyst composition of the present invention consists essentially of vitrified silica, which is preferably used in the form of glass beads, such as beads having average diameters ranging from about 1 to about 10 mm.

Catalytic Treatment of Tertiary Butyl Alcohol

In accordance with the present invention, a tertiary butyl alcohol feedstock, as above described, is brought into contact with a catalyst of the present invention under reaction conditions correlated to substantially selectively catalytically convert the tertiary butyl hydroperoxide, the ditertiary butyl peroxide and the allyl tertiary butyl peroxide contaminants in the tertiary butyl alcohol feedstock to decomposition products, principally tertiary butyl alcohol with not more than a minor increase in the level of contamination of any acetone, methanol and isobutylene that may be present in the tertiary butyl alcohol as contaminants.

The reaction should be conducted on a continuous basis by passing the tertiary butyl alcohol through a reactor containing a bed of a catalyst of the present invention under reaction conditions including a temperature within the range of about 160° to about 200° C. The reaction is preferably conducted at 200 to 800 psig., although pressures of about 0 to about 2000 psig. may be used if desired. The tertiary butyl alcohol should be passed over the bed of catalyst at a liquid hourly space velocity of about 0.5 to about 4.

The reaction product, after being degassed, is suitable for use as an octane-enhancing component of motor fuel, such as gasoline.

Thus, for example, the effluent from the reactor may be passed through a phase separation zone in order to permit gaseous reaction components including hydrogen and isobutane to volatilize from the product to thereby provide the desired reaction product.

The specific correlation of conditions to be utilized with any specific catalyst of the present invention can be determined by one of ordinary skill in the art with comparative ease. Thus, for example, the tertiary butyl alcohol feedstock should be analyzed prior to catalytic treatment to determine the level of contamination by tertiary butyl hydroperoxide, ditertiary butyl peroxide, acetone, methanol and isobutylene. If there is an insufficient reduction of the peroxides such that a significant amount (e.g., more than about 0.1 wt. %) of tertiary butyl hydroperoxide and/or ditertiary butyl peroxide is still present, the reaction conditions are not sufficiently severe, and should be increased such as, for example, by increasing reaction temperature or contact time in order to obtain the desired reduction of the tertiary butyl hydroperoxide.

If, on the other hand, there is a significant increase in the level of contamination of acetone, isobutylene and/or methanol, the reaction conditions are too severe for the particular catalyst and the reaction conditions should be ameliorated (e.g., by reducing contact time or temperature).

WORKING EXAMPLES

Reactors

Reactor (300 cc)

The reactor was a stainless steel tube (1"×30") which was electrically heated. The catalyst bed was 300 cc. Liquid feed was pumped into the bottom of the reactor. Pressure regulation was with a Skinner Uni-Flow valve and a Foxboro controller. The liquid feed was pumped with a Ruska dual drive pump.

Reactor (100 cc)

The reactor was a stainless steel tube (0.51×29") which was electrically heated. The catalyst bed (if any) was 100 cc. Liquid was pumped into the bottom of the reactor. Pressure regulation was with a Skinner Uni-Flow valve and a Foxboro controller. The liquid feed was pumped with a Ruska dual drive pump.

Feed

The feed was a crude TBA stream from the PO pilot plant which was enriched with commercial DTBP. This feed then contained about 0.8% DTBP, 0.4% ATBP, 97% TBA and various other impurities.

Thermal Decomposition

Data on the thermal decomposition of dilute solutions of peroxides were generated at 160° to 200° C. and space velocities of 1.0 to 2.0. Data are shown in the following tables.

TABLE I

Catalytic Decomposition of DTBP in a Continuous Reactor

| Notebook Number | 6844-89FD | 6844-92-1 | 6844-92-2 | 6844-92-3 |
|---|---|---|---|---|
| Catalyst |  | 1 mm Glass Beads | 1 mm Glass Beads | 1 mm Glass Beads |
| Reactor (300 cc) |  | 150 | 150 | 150 |
| Pressure (psig) |  | 500 | 500 | 500 |
| Feed Rate (cc/hr) |  | 150 | 150 | 150 |
| Temperature (°C.) |  | 160 | 180 | 200 |
| Time on Stream (hr) |  | 4 | 4 | 4 |
| Space Vel. (cc/cc) |  | 1.0 | 1.0 | 1.0 |
| DTBP Conv. (%) |  | 97.7 | 99.1 | 99.1 |
| ATBP Conv. (%) |  | 100.0 | 99.4 | 99.7 |
| TBA Conversion (%) |  | 0.0 | 0.0 | 0.0 |
| Composition |  |  |  |  |
| IC4 | 0.002 | 0.007 | 0.032 | 0.056 |
| MEOH/MF | 0.103 | 0.106 | 0.107 | 0.108 |
| Acetone | 1.214 | 1.780 | 1.828 | 1.841 |
| TBA | 96.600 | 97.274 | 97.231 | 97.083 |
| DTBP | 0.703 | 0.016 | 0.006 | 0.006 |
| IPHP/ATBP | 0.360 | 0.000 | 0.002 | 0.001 |

TABLE II

Catalytic Decomposition of DTBP in a Continuous Reactor

| Notebook Number | 6844-89FD | 684492B-1 | 684492B-2 | 684492B-3 |
|---|---|---|---|---|
| Catalyst |  | 1 mm Glass Beads | 1 mm Glass Beads | 1 mm Glass Beads |
| Reactor (300 cc) |  | 150 | 150 | 150 |
| Pressure (psig) |  | 500 | 500 | 500 |
| Feed Rate (cc/hr) |  | 300 | 300 | 300 |
| Temperature (°C.) |  | 160 | 180 | 190 |
| Time on Stream (hr) |  | 4 | 4 | 4 |
| Space Vel. (cc/cc) |  | 2.0 | 2.0 | 2.0 |
| DTBP Conv. (%) |  | 80.5 | 99.1 | 99.1 |
| ATBP Conv. (%) |  | 99.7 | 100.0 | 99.7 |
| TBA Conversion (%) |  | 0.0 | 0.0 | 0.0 |
| Composition |  |  |  |  |
| IC4 | 0.002 | 0.005 | 0.012 | 0.012 |
| MEOH/MF | 0.103 | 0.110 | 0.108 | 0.108 |
| Acetone | 1.214 | 1.696 | 1.825 | 1.800 |
| TBA | 96.600 | 97.212 | 97.199 | 97.229 |
| DTBP | 0.703 | 0.137 | 0.006 | 0.006 |
| IPHP/ATBP | 0.360 | 0.001 | 0.000 | 0.001 |

TABLE III

Catalytic Decomposition of DTBP in a Continuous Reactor

| Notebook Number | 6844-89FD | 6844-89-1 | 6844-89-2 | 6844-89-3 |
|---|---|---|---|---|
| Catalyst |  | 3 mm Glass Beads | 3 mm Glass Beads | 3 mm Glass Beads |
| Reactor (300 cc) |  | 125 | 125 | 125 |
| Pressure (psig) |  | 500 | 500 | 500 |
| Feed Rate (cc/hr) |  | 125 | 125 | 125 |
| Temperature (°C.) |  | 160 | 180 | 200 |
| Time on Stream (hr) |  | 4 | 4 | 4 |
| Space Vel. (cc/cc) |  | 1.0 | 1.0 | 1.0 |
| DTBP Conv. (%) |  | 72.3 | 97.4 | 99.4 |
| ATBP Conv. (%) |  | 98.6 | 100.0 | 100.0 |
| TBA Conversion (%) |  | 0.0 | 0.0 | 0.0 |
| Composition |  |  |  |  |
| IC4 | 0.002 | 0.000 | 0.009 | 0.019 |
| MEOH/MF | 0.103 | 0.113 | 0.110 | 0.115 |
| Acetone | 1.214 | 1.545 | 1.713 | 1.768 |
| TBA | 96.600 | 97.166 | 97.160 | 97.083 |
| DTBP | 0.703 | 0.195 | 0.018 | 0.004 |
| IPHP/ATBP | 0.360 | 0.005 | 0.000 | 0.000 |

TABLE IV

Catalytic Decomposition of DTBP in a Continuous Reactor

| Notebook Number | 6844-89FD | 6844-90-1 | 6844-90-2 | 6844-90-3 |
|---|---|---|---|---|
| Catalyst |  | 6 mm Glass Beads | 6 mm Glass Beads | 6 mm Glass Beads |
| Reactor (300 cc) |  | 125 | 125 | 125 |
| Pressure (psig) |  | 500 | 500 | 500 |
| Feed Rate (cc/hr) |  | 125 | 125 | 125 |
| Temperature (°C.) |  | 160 | 180 | 200 |
| Time on Stream (hr) |  | 4 | 4 | 4 |
| Space Vel. (cc/cc) |  | 1.0 | 1.0 | 1.0 |
| DTBP Conv. (%) |  | 55.9 | 91.7 | 99.4 |
| ATBP Conv. (%) |  | 96.9 | 99.7 | 100.0 |
| TBA Conversion (%) |  | 0.0 | 0.0 | 0.0 |
| Composition |  |  |  |  |
| IC4 | 0.002 | 0.004 | 0.006 | 0.017 |
| MEOH/MF | 0.103 | 0.113 | 0.113 | 0.115 |
| Acetone | 1.214 | 1.421 | 1.680 | 1.762 |
| TBA | 96.600 | 97.140 | 97.174 | 97.091 |
| DTBP | 0.703 | 0.310 | 0.058 | 0.004 |
| IPHP/ATBP | 0.360 | 0.011 | 0.001 | 0.000 |

TABLE V

Catalytic Decomposition of DTBP in a Continuous Reactor

| Notebook Number | 6844-89FD | 684490B-1 | 684490B-2 | 684490B-3 |
|---|---|---|---|---|
| Catalyst |  | 6 mm Glass Beads | 6 mm Glass Beads | 6 mm Glass Beads |
| Reactor (300 cc) |  | 125 | 125 | 125 |
| Pressure (psig) |  | 500 | 500 | 500 |
| Feed Rate (cc/hr) |  | 250 | 250 | 250 |
| Temperature (°C.) |  | 160 | 180 | 190 |
| Time on Stream (hr) |  | 4 | 4 | 4 |
| Space Vel. (cc/cc) |  | 2.0 | 2.0 | 2.0 |
| DTBP Conv. (%) |  | 75.4 | 100.0 | 100.0 |
| ATBP Conv. (%) |  | 99.2 | 100.0 | 100.0 |
| TBA Conversion (%) |  | 0.0 | 0.0 | 0.0 |
| Composition |  |  |  |  |
| IC4 | 0.002 | 0.005 | 0.012 | 0.015 |
| MEOH/MF | 0.103 | 0.107 | 0.108 | 0.108 |
| Acetone | 1.214 | 1.595 | 1.775 | 1.777 |
| TBA | 96.600 | 97.268 | 97.248 | 97.246 |
| DTBP | 0.703 | 0.173 | 0.000 | 0.000 |
| IPHP/ATBP | 0.360 | 0.003 | 0.000 | 0.000 |

TABLE VI

Catalytic Decomposition of DTBP in a Continuous Reactor

| Notebook Number | 6844-89FD | 6844-93-1 | 6844-93-2 | 6844-93-3 |
|---|---|---|---|---|
| Catalyst |  | 10 mm Glass Beads | 10 mm Glass Beads | 10 mm Glass Beads |
| Reactor (300 cc) |  | 150 | 150 | 150 |
| Pressure (psig) |  | 500 | 500 | 500 |
| Feed Rate (cc/hr) |  | 150 | 150 | 150 |
| Temperature (°C.) |  | 160 | 180 | 190 |
| Time on Stream (hr) |  | 4 | 4 | 4 |
| Space Vel. (cc/cc) |  | 1.0 | 1.0 | 1.0 |
| DTBP Conv. (%) |  | 93.7 | 100.0 | 100.0 |
| ATBP Conv. (%) |  | 99.7 | 99.7 | 99.7 |
| TBA Conversion (%) |  | 0.0 | 0.0 | 0.0 |
| Composition |  |  |  |  |
| IC4 | 0.002 | 0.004 | 0.017 | 0.050 |
| MEOH/MF | 0.103 | 0.237 | 0.125 | 0.114 |
| Acetone | 1.214 | 1.729 | 1.767 | 1.797 |
| TBA | 96.600 | 97.200 | 97.313 | 97.250 |
| DTBP | 0.703 | 0.044 | 0.000 | 0.000 |
| IPHP/ATBP | 0.360 | 0.001 | 0.001 | 0.001 |

TABLE VII

Catalytic Decomposition of DTBP in a Continuous Reactor

| Notebook Number | 6844-89FD | 684493B-1 | 684493B-2 | 684493B-3 |
|---|---|---|---|---|
| Catalyst |  | 10 mm Glass Beads | 10 mm Glass Beads | 10 mm Glass Beads |
| Reactor (300 cc) |  | 150 | 150 | 150 |
| Pressure (psig) |  | 500 | 500 | 500 |
| Feed Rate (cc/hr) |  | 300 | 300 | 300 |
| Temperature (°C.) |  | 160 | 180 | 190 |
| Time on Stream (hr) |  | 4 | 4 | 4 |
| Space Vel. (cc/cc) |  | 2.0 | 2.0 | 2.0 |
| DTBP Conv. (%) |  | 58.0 | 94.3 | 100.0 |
| ATBP Conv. (%) |  | 96.7 | 100.0 | 100.0 |
| TBA Conversion (%) |  | 0.0 | 0.0 | 0.0 |
| Composition |  |  |  |  |
| IC4 | 0.002 | 0.004 | 0.006 | 0.010 |
| MEOH/MF | 0.103 | 0.109 | 0.108 | 0.108 |
| Acetone | 1.214 | 1.538 | 1.762 | 1.785 |
| TBA | 96.600 | 97.226 | 97.269 | 97.239 |
| DTBP | 0.703 | 0.295 | 0.040 | 0.000 |
| IPHP/ATBP | 0.360 | 0.012 | 0.000 | 0.000 |

TABLE VIII

Catalytic Decomposition of DTBP in a Continuous Reactor

| Notebook Number | 6844-89FD | 6844-91-1 | 6844-91-2 | 6844-91-3 |
|---|---|---|---|---|
| Catalyst |  | Empty Reactor | Empty Reactor | Empty Reactor |
| Reactor (300 cc) |  | 300 | 300 | 300 |
| Pressure (psig) |  | 500 | 500 | 500 |
| Feed Rate (cc/hr) |  | 300 | 300 | 300 |
| Temperature (°C.) |  | 160 | 180 | 200 |
| Time on Stream (hr) |  | 4 | 4 | 4 |
| Space Vel. (cc/cc) |  | 1.0 | 1.0 | 1.0 |
| DTBP Conv. (%) |  | 38.0 | 92.3 | 98.7 |
| ATBP Conv. (%) |  | 87.5 | 99.4 | 99.7 |
| TBA Conversion (%) |  | 0.0 | 0.0 | 0.0 |
| Composition |  |  |  |  |
| IC4 | 0.002 | 0.003 | 0.006 | 0.010 |
| MEOH/MF | 0.103 | 0.114 | 0.116 | 0.116 |
| Acetone | 1.214 | 1.321 | 1.682 | 1.737 |
| TBA | 96.600 | 97.088 | 97.179 | 97.144 |
| DTBP | 0.703 | 0.436 | 0.054 | 0.009 |
| IPHP/ATBP | 0.360 | 0.045 | 0.002 | 0.001 |

TABLE IX

Catalytic Decomposition of DTBP in a Continuous Reactor
(Empty Tube)

| Notebook Number | 6844-40-2 | 6844-72-1 | 6844-72-2 | 6844-72-3 |
|---|---|---|---|---|
| Catalyst |  | None | None | None |
| Reactor (cc) |  | 300 | 300 | 300 |
| Pressure (psig) |  | 300 | 300 | 300 |
| Feed Rate (cc/hr) |  | 600 | 600 | 600 |
| Temperature (°C.) |  | 170 | 180 | 190 |
| Time on Stream (hr) |  | 4 | 4 | 4 |
| Space Vel. (cc/cc) |  | 2.0 | 2.0 | 2.0 |
| DTBP Conv. (%) |  | 67.5 | 84.9 | 95.0 |
| ATBP Conv. (%) |  | 97.3 | 99.0 | 99.5 |
| TBA Conversion (%) |  | 0.0 | 0.0 | 0.0 |
| Composition |  |  |  |  |
| IC4 | 0.002 | 0.011 | 0.011 | 0.012 |
| MEOH/MF | 0.036 | 0.054 | 0.051 | 0.052 |
| Acetone | 0.216 | 0.926 | 1.067 | 1.166 |
| TBA | 96.864 | 97.173 | 97.214 | 97.212 |
| DTBP | 0.966 | 0.314 | 0.146 | 0.048 |
| IPHP/ATBP | 0.415 | 0.011 | 0.004 | 0.002 |

Appropriate data taken from Tables I through IX show clearly that glass beads have a weak-moderate effect on the decomposition of peroxides (in particular DTBP).

| Glass Beads Diameter, mm | Conv. DTBP (%) (Calculated) |
| --- | --- |
| 1.0 | 97.7 |
| 3.0 | 72.3 |
| 6.0 | 55.9 |
| 10.0 | 93.7 |
| None | 38.0 |

The decomposition is faster in the presence of glass beads than in an empty reactor. This allows the decomposition to be conducted at lower temperatures. Since more TBA (and less acetone) is formed at lower temperatures, the process may be conducted at lower temperatures.

The foregoing examples are given by way of illustration only, and are not intended as limitations on the scope of this invention, as defined by the appended claims.

Having thus described our invention, what is claimed is:

1. In a method for enhancing the motor fuel quality of a tertiary butyl alcohol feedstock contaminated with tertiary butyl hydroperoxide, ditertiary butyl hydroperoxide and allyl tertiary butyl peroxide, the improvement comprising the steps of:
   a. continuously contacting said feedstock in a reaction zone with a catalyst at a temperature of about 100° to about 200° C. for a period of time sufficient to substantially decompose said tertiary butyl hydroperoxide, said ditertiary butyl hydroperoxide and said allyl tertiary butyl peroxide and
   b. recovering from the products of said reaction a tertiary butyl alcohol product containing not more than about 100 ppm of tertiary butyl hydroperoxide and not more than about 100 ppm of ditertiary butyl peroxide,
   c. said catalyst consisting essentially of vitrified silica.

2. A method as in claim 1 wherein the vitrified silica is used in the form of glass beads.

3. A method for enhancing the motor fuel quality of a tertiary butyl alcohol feedstock contaminated with from about 0.0 to about 1.0 wt. % of tertiary butyl hydroperoxide and from about 0.1 to about 5 wt. % of ditertiary butyl peroxide, which comprises the steps of:
   a. catalytically contacting said feedstock in a reaction zone at a temperature of about 160°-200° C. for a time sufficient to substantially completely decompose said tert. butyl hydroperoxide and ditert. butyl peroxide, and
   b. recovering from the products of said reaction a tertiary butyl alcohol containing not more than about 100 ppm of tertiary butyl hydroperoxide and not more than about 100 ppm of ditertiary butyl peroxide, and
   c. using, as said catalyst, a catalyst consisting essentially of glass beads.

4. A method as in claim 2 wherein the reaction conditions also include a pressure of about 0 to about 2,000 psig. and wherein the said feedstock is passed through a tubular reactor containing said glass beads at the rate of about 1 to about 4 volumes of said feedstock per volume of said reactor per hour.

* * * * *